United States Patent
Kwak et al.

(10) Patent No.: US 6,620,521 B1
(45) Date of Patent: Sep. 16, 2003

(54) WATER-RESISTANT COLOR INKJET RECEPTIVE FILMS

(75) Inventors: Yoon Tae Kwak, Woodcliff Lake, NJ (US); Stephen L. Kopolow, Plainsboro, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/663,010

(22) Filed: Sep. 15, 2000

(51) Int. Cl.[7] ............... C08J 7/04; C08F 26/10
(52) U.S. Cl. ............... 428/475.2; 428/474.4; 428/500; 526/264
(58) Field of Search ............... 428/475.2, 500, 428/474.4; 626/264

(56) References Cited

U.S. PATENT DOCUMENTS 5,321,110 A * 6/1994 Shih ............... 526/264
5,608,021 A * 3/1997 Uchiyama et al. ........ 526/210
6,193,961 B1 * 2/2001 Liu et al. ............... 424/70.12

FOREIGN PATENT DOCUMENTS

JP 06-316510 A * 11/1994

* cited by examiner

*Primary Examiner*—D. R. Wilson
(74) *Attorney, Agent, or Firm*—Walter Katz; William J. Davis; Marilyn J. Maue

(57) ABSTRACT

What is described herein is a process for preparing a lightly-crosslinked copolymer of (a) vinyl pyrrolidone (VP) and (b) dimethylaminopropyl methacrylamide (DMAPMA) under more reproducible conditions. Suitably the weight ratio of (a):(b) is 50–95:50–5, preferably 80:20. The copolymer has a Brookfield viscosity of 5,000 to 45,000 cps; preferably 10,000 to 30,000 cps, and a haze of <100 NTU; it includes about 0.1 to 0.5 wt. %, preferably 0.2 to 0.4 wt. %, of a cross-linking agent based upon the total weight of the monomers in the copolymer.

6 Claims, No Drawings

WATER-RESISTANT COLOR INKJET RECEPTIVE FILMS

CROSS-REFERENCE TO RELATED PATENT APPLICATIONS

This application is related to co-pending U.S. patent application Ser. No. 09/573,805, filed May 18, 2000.

BACKGROUND OF THE INVENTION

1. Field of the Invention

This invention relates to color inkjet recording films, and, more particularly, to water-resistant color-receptive films coated with lightly crosslinked copolymers of vinyl pyrrolidone (VP) and dimethylaminopropyl methacrylamide (DMAPMA).

2. Description of the Prior Art

The advent of color inkjet printing has been instrumental in fueling the print-on-demand revolution and has also created a number of challenges. Often, the surface of the desired media does not possess the necessary properties for accepting the ink-jet ink. This results in long dry times and/or a poor ink-jet image. It has long been recognized that a surface treatment or media coating plays a critical role in the final print quality. Numerous media coatings are known in the art. They may contain any number of components and often consist of more than one layer. These ink-receptive coatings generally contain at least one hydrophilic polymer; often poly(vinylpyrrolidone) (PVP). PVP brings many benefits to properly formulated media coatings including rapid ink dry time, excellent print quality, highly resolved circular dots, and high, uniform optical density. Furthermore, copolymers of vinylpyrrolidone (VP) along with other suitable comonomers, such as dimethylaminoethyl methacrylamide (DMAPMA), acrylic acid, or vinyl acetate, have been used separately or in conjunction with PVP, to further optimize performance. However, it is desired also to provide long-term, excellent water-resistant qualities for such films.

SUMMARY OF THE INVENTION

What is described herein is a process for preparing a lightly-crosslinked copolymer of (a) vinyl pyrrolidone (VP) and (b) dimethylaminopropyl methacrylamide (DMAPMA) under more reproducible conditions. Suitably the weight ratio of (a):(b) is 50–90:50–5, preferably 80:20. The copolymer has a Brookfield viscosity of 5,000 to 45,000 cps; preferably 10,000 to 30,000 cps, and a haze of <100 NTU; it includes about 0.1 to 0.5 wt. %, preferably 0.2 to 0.4 wt. %, of a cross-linking agent based upon the total weight of monomers in the copolymer.

Preferably the crosslinking agent is pentaerythritol triallyl ether (PETE), and the polymerization initiator is an azo-type initiator.

The ink-receptive film of the invention is capable of being printed from a color inkjet printer to form superior water-resistant color images thereon.

DETAILED DESCRIPTION OF THE INVENTION

EXAMPLES 1–3

Process Examples

Example 1

1. To a 2-l kettle fitted with a nitrogen inlet tube, thermocouple, agitator, and feed lines is added 87.15 g of vinyl pyrrolidone HPVP, 697 g DI water of 0.275 g (0.25% based upon monomer) pentaerythritol triallyl ether.
2. Purge with nitrogen subsurface for 30 minutes.
3. Heat to 70° C.
4. In a separate container weigh out 22.69 g DMAPMA.
5. When kettle temperature is at 70° C., stop subsurface nitrogen purge and purge above surface. Precharge 1.1 g DMAPMA from container.
6. Start continuous addition of the remaining DMAPMA (21.86 g) over 210 minutes. Flow rate 0.1 ml/minute. Once DMAPMA flow started initiate with first shot of Vazo® 67 in isopropanol IPA (Time 0).
7. Initiator is added in 5 shots at 0, 30, 60, 150, and 210 minutes. 0.2 grams of Vazo® 67 in 1.0 g IPA is added for each shot and two 0.5 g IPA washes are made.
8. Hold the reaction temperature overnight at 70° C.
9. When VP is below 400 ppm dilute the batch with 266.7 g DI water.
10. Cool batch to 50° C.
11. Neutralize the batch with conc. HCl to pH of 6.2 to 6.8 at 50° C. Room temperature pH will be 6.8 to 7.2. Requires approximately 14 g of conc. HCl.
12. Add 0.15 to 0.19% of preservative.

Example 2

1. To a 2-l kettle fitted with a nitrogen inlet tube, thermocouple, agitator, and feed lines is added 87.15 g of HPVP, 697 g DI water and 0.275 g (0.25% based upon monomer) pentaerythritol triallyl ether.
2. Purge with nitrogen subsurface for 30 minutes.
3. Heat to 70° C.
4. In a separate container weigh out 22.69 g DMAPMA.
5. When kettle temperature is at 70° C., stop subsurface nitrogen purge and purge above surface. Precharge 1.1 g DMAPMA from container.
6. Start continuous addition of the remaining DMAPMA (21.86 g) over 210 minutes. Flow rate 0.1.1 ml/minute. Once DMAPMA flow started initiate with first shot of Vazo® 67 in IPA (Time 0).
7. Initiator is added in 5 shots at 0, 30, 60, 150, and 210 minutes. 0.3 grams of Vazo® 67 in 1.0 g IPA is added for each shot and two 0.5 g IPA washes are made.
8. Hold the reaction temperature overnight at 70° C.
9. When VP is below 400 ppm dilute the batch with 266.7 g DI water.
10. Cool batch to 50° C.
11. Neutralize the batch with conc. HCl to pH of 6.2 to 6.8 at 50° C. Room temperature pH will be 6.8 to 7.2. Requires approximately 14 g of conc. HCl.
12. Add 0.15 to 0.19% of preservative.

Example 3

1. To a 2-l kettle fitted with a nitrogen inlet tube, thermocouple, agitator, and feed lines is added 87.15 g of HPVP, 630 g DI water and 0.33 g (0.3% based upon monomer) pentaerythritol triallyl ether.
2. Purge with nitrogen subsurface for 30 minutes.
3. Heat to 70° C.
4. In a separate container weigh out 22.69 g DMAPMA and 67 g DI water. Purge with nitrogen 30 minutes. Continue nitrogen purge while feeding.
5. When kettle temperature is at 70° C., stop subsurface nitrogen purge and purge above surface. Precharge 4.23 g DMAPMA/water from container.
6. Start continuous addition of the remaining DMAPMA water (85.46 g) over 210 minutes. Flow rate 0.40 ml/minute. Once DMAPMA/water flow started initiate with first shot of Vazo® 67 in IPA (Time 0).

7. Initiator is added in 5 shots at 0, 30, 60, 150, and 210 minutes. 0.4 grams of Vazo® 67 in 1.0 g IPA is added for each shot and two 0.5 g IPA washes are made.
8. Hold the reaction temperature overnight at 70° C.
9. When VP is below 400 ppm dilute the batch with 266.7 g DI water.
10. Cool batch to 50° C.
11. Neutralize the batch with conc. HCl to pH of 6.2 to 6.8 at 50° C. Room temperature pH will be 6.8 to 7.2. Requires approximately 14 g of conc. HCl.
12. Add 0.15 to 0.19% of preservative.

Test Methods

Drawdowns from a 10% aqueous solution of the polymer were cast onto a polyester substrate using a #38 Mayer bar and allowed to dry in an oven at 100° C. to give a dry coating thickness of ~9 micron.

Coated samples were then printed using a HP 832C printer at 600 DPI in "HP Premium Photo Paper" mode. Individual blocks of cyan(C), magenta(M), yellow(Y), and black(K), approximately 1"×1.75" in size, were printed side by side. Small blocks of C, M, Y, and K, approximately ⅛"×¼", are printed repeatedly down one edge of the page to provide a built-in time-line for measuring off-set time as described below.

Off-set time is the minimum time required for no ink to transfer to a cover sheet placed on top of the print when contacted with a 4-lb roller immediately after printing. Ink transfer is determined at the point where the OD after testing dropped by a value of 0.2 units. For off-set times are most desirable.

Water-resistance was measured by the standard test procedure set forth below*.

* Water resistance was tested by placing the printed sheet at a 45° angle and dripping 10 ml of water at a constant rate (2 ml/min) over the surface for a maximum of 5 minutes. The samples were then judged by following rating system:
Poor—All ink removed in less than 1 minute.
Fair—Most or all ink removed between 1 and 5 minutes.
Moderate—Some (<50%) loss of ink after 5 minutes.
Good—Very slight (<10%) loss of ink with minimal running.
Very Good—100% water resistance with no change in appearance.

Results

The results of these tests, shown in Table 1 below, establish that the lightly-crosslinked VP/DMAPMA copolymer exhibits an advantageous water-resistant property as well as desired viscosity and haze properties.

The crosslinker suitably is a di-, tri- or poly-functional crosslinking agent, such as pentaerythritol triallyl ether (PETE); diethylene glycol di(meth)acrylate; triethylene glycol di(meth)acrylate; or polyethyleneglycol di(meth)acrylate.

The polymerization initiators suitably is an azo type such as Vazo® 52, 64 or 67.

TABLE 1

| Ex. No. | X-Linker* (%) | Initiator** (g/shot) | VP (ppm) | Haze (NTU)*** | VISC (cps) | WATER-PROOF (min) |
|---|---|---|---|---|---|---|
| 1 | 0.25 | 0.2 | 139 | | 28200 | 10 |
| 2 | 0.25 | 0.3 | 151 | 25.2 | 13000 | 11 |
| 3 | 0.3 | 0.4 | 173 | 45.7 | 12800 | 7.12 |

*Based on total monomers
**A total of 5 shots
***NTU = nephelometric turbidity unit
The offset times of Examples 1–3 were <1 minute.

While the invention has been described with particular reference to certain embodiments thereof, it will be understood that changes and modifications may be made which are within the skill of the art. Accordingly, it is intended to be bound only by the following claims, in which:

What is claimed is:

1. A water-resistant, color inkjet-receptive film having coated thereon a lightly-crosslinked copolymer of (a) vinyl pyrrolidone (VP) and (b) dimethylaminopropyl methacrylamide (DMAPMA) in a weight ratio of a:b of 50–95:50–5 having a crosslinking agent present in said copolymer in an amount of about 0.1–0.5 wt. % based upon the total weight of monomers in the copolymer which copolymer has a Brookfield viscosity of 5,000 to 45,000 cps (20° C., Spindle #7, Speed 20, 10% aqueous solution).

2. A water-resistant, color inkjet-receptive film according to claim 1 wherein the weight ratio of (a):(b) is 80:20.

3. A water-resistant, color inkjet-receptive film according to claim 1 in which said viscosity is 10,000 to 30,000 cps.

4. A water-resistant, color inkjet-receptive film according to claim 1 wherein said crosslinking agent is present in said copolymer in an amount of 0.2–0.4 wt. %.

5. A water-resistant, color inkjet-receptive film according to claim 1 wherein said crosslinking agent is pentaerythritol triallyl ether (PETE).

6. A water-resistant, color inkjet-receptive film according to claim 1 wherein said film is a polyester.

* * * * *